(12) United States Patent
Horton

(10) Patent No.: US 7,806,749 B2
(45) Date of Patent: *Oct. 5, 2010

(54) COSMETIC APPLIANCE AND METHOD OF USE

(75) Inventor: Denise Horton, Westlake Village, CA (US)

(73) Assignee: Bring It Up, Inc., Calabasas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/348,183

(22) Filed: Jan. 2, 2009

(65) Prior Publication Data

US 2009/0111357 A1 Apr. 30, 2009

Related U.S. Application Data

(63) Continuation of application No. 11/953,085, filed on Dec. 10, 2007, which is a continuation of application No. 10/170,302, filed on Jun. 12, 2002, now abandoned.

(51) Int. Cl.
*A41C 3/00* (2006.01)

(52) U.S. Cl. ............................. 450/81; 450/37
(58) Field of Classification Search ............... 450/81, 450/54–58, 36–28; 424/449, 448; 602/41, 602/42, 58
See application file for complete search history.

(56) References Cited

U.S. PATENT DOCUMENTS

| | | | | |
|---|---|---|---|---|
| 4,553,550 A * | 11/1985 | Hattori | .................. | 450/81 |
| 4,640,288 A * | 2/1987 | Hattori | .................. | 450/81 |
| 6,200,195 B1 * | 3/2001 | Furuno et al. | .............. | 450/81 |
| 6,371,831 B1 * | 4/2002 | Dodge | .................. | 450/81 |
| 7,473,158 B2 * | 1/2009 | Horton | .................. | 450/81 |

\* cited by examiner

*Primary Examiner*—Gloria Hale
(74) *Attorney, Agent, or Firm*—Lewis Brisbois Bisgaard & Smith LLP

(57) ABSTRACT

A cosmetic appliance and method of use for temporarily lifting, supporting or smoothing the skin of selected areas of a user's body, including the eyebrows, eyelids, throat, neck, breasts and other areas, and which is not readily apparent once applied, formed in predetermined shapes from thin, generally translucent flexible sheeting to one side of which adhesive has been applied and covered with a peel-away layer.

5 Claims, 3 Drawing Sheets

COSMETIC APPLIANCE AND METHOD OF USE

The present application is a continuation of application Ser. No. 11/953,085, filed Dec. 10, 2007, which is a continuation of application Ser. No. 10/170,302, filed Jun. 12, 2002, now abandoned.

FIELD OF INVENTION

The present invention is directed to a cosmetic appliance and method for temporarily altering the appearance and shape of selected areas of the surface of a user's body by lifting and/or supporting a selected area of skin and underlying tissue and/or smoothing the surface of the of the skin of a selected area of the user's body.

SUMMARY OF INVENTION

The cosmetic appliance is formed of a thin, generally translucent flexible sheet, to one side of which an adhesive has been applied and covered with a peel-away layer. The appliance is cut into predetermined shapes which vary in size, and shape, depending upon the intended area of use upon the body, as well as upon the size of the user's anatomy. It is to be understood and emphasized that a variety of shapes of the appliance may be used to accomplish the desired purpose of lifting and/or smoothing the skin. The appliance may be cut from a conventional gas permeable, pressure sensitive adhesive tape, an example of which is 3M Transpore tape.

A general description of the appliance and its functions are as follows. The appliance is adapted to provide support and to lift saggy areas of a user's skin and immediately underlying tissue at selected areas, including, for example, the forehead, eyebrows, temples/eye area, cheeks, chin, neck and breasts. The appliance is utilized by first selecting an appliance of appropriate shape and size. Next, the peel-away backing is removed from a portion (or optionally, from all) of the appliance to expose the adhesive. Thereafter, a portion of the exposed adhesive surface of the appliance is applied to the skin at a predetermined location and pressure applied to promote adhesion between the appliance and the skin. The adhered appliance is then gently moved in such a manner and direction as to cause the adjacent skin to be lifted and/or smoothed to the degree desired by the user. With the appliance in the desired position, the remainder of adhesive is exposed (unless it was optionally exposed initially) and the free or unadhered portion of the appliance is pressed onto the skin to complete its application. With the appliance thus applied, the skin adjacent to the appliance is held in the position desired by the user. Because the appliance is thin, that is of a few mils in thickness, with 1.7 mils being a preferred thickness, and because it is translucent, the appliance may easily be made less detectable by concealing the appliance with cosmetic preparations, if desired.

BRIEF DESCRIPTION OF DRAWINGS

The foregoing aspects and the attendant advantages of the present cosmetic appliances will become more readily appreciated by reference to the following detailed description, when taken in conjunction with the accompanying drawings, wherein.

DETAILED DESCRIPTION OF PREFERRED EMBODIMENTS

FIG. 1 Embodiment

Figure 1:
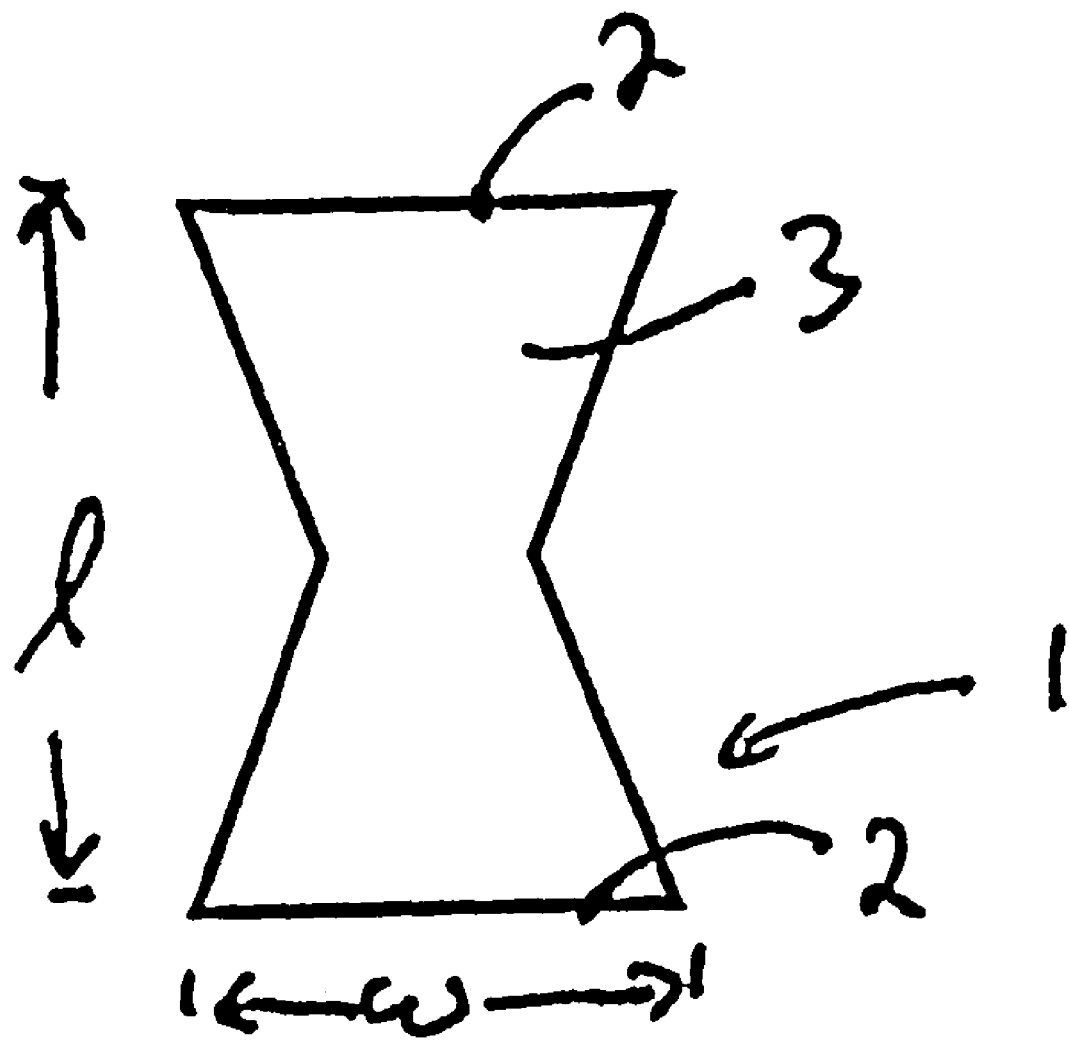
FIG. 1 is a top view of a preferred embodiment cosmetic appliance described herein.

An example of a preferred embodiment of the appliance intended for use in lifting and smoothing the skin adjacent to the eyebrows is shown in FIG. 1. With reference to FIG. 1, the appliance (1) has a generally hourglass shape, that is the width (w) at the mid-point along the length (l) is less than at either end (2). The preferred length (l) is approximately 1 inch, but include lengths of less than 1 inch and up to about 2 inches. The appliance includes a top surface (3) and bottom surface (4) (not shown) having an adhesive surface covered with a peel-away layer (5) (not shown).

FIG. 2 Embodiment

Figure 2:
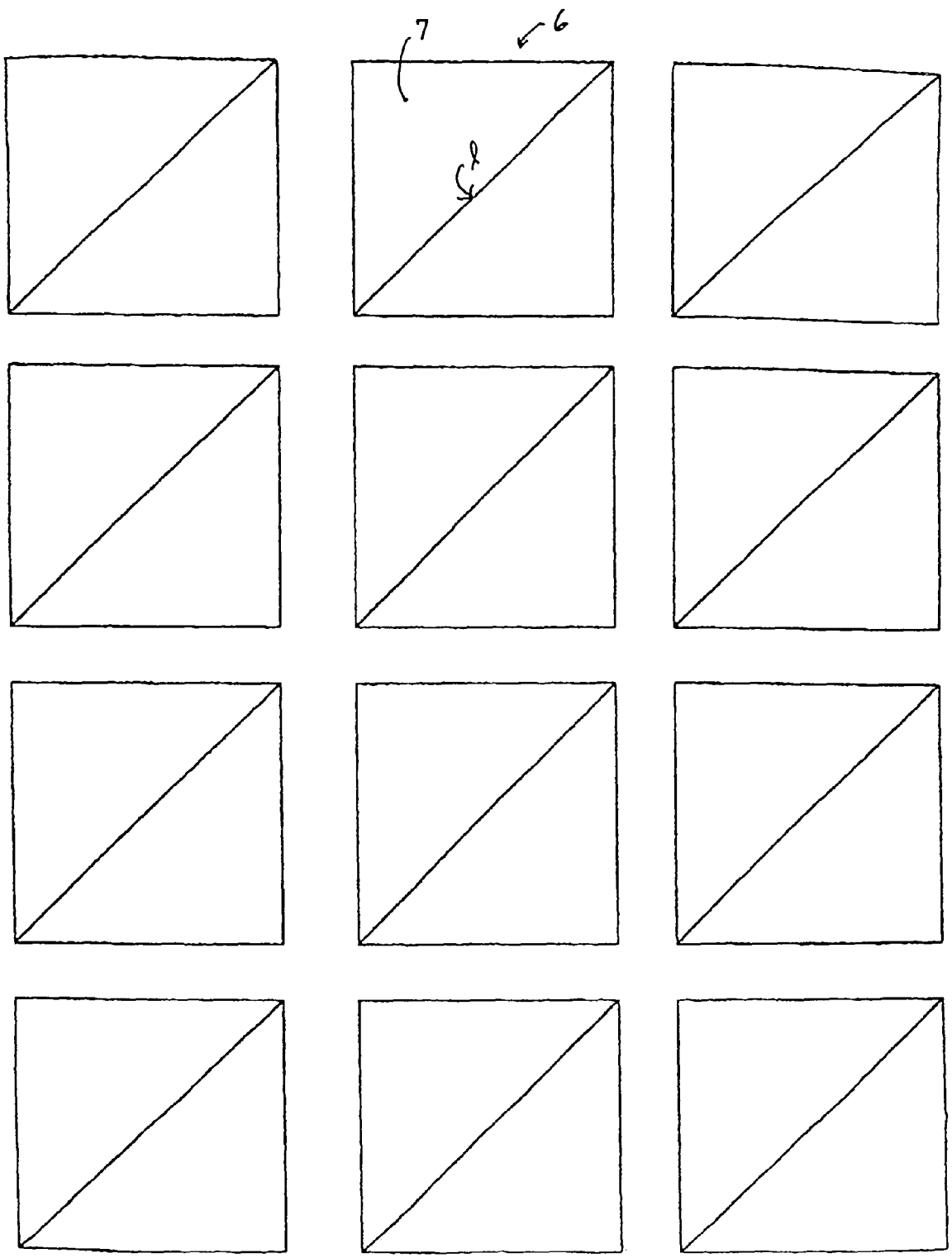
FIG. 2 is a top view of an alternate preferred embodiment cosmetic appliance described herein; and, FIG. 3 is a bottom view of another alternate preferred embodiment cosmetic appliance described herein.

An example of a preferred embodiment of the appliance intended for use in lifting and smoothing the skin adjacent to the throat, chin or neck area is shown in FIG. 2. With reference to FIG. 2, the appliance (6) has a generally triangle shape, with two such triangles provided on the same cut-out. The shape of the triangle may vary, with an isosceles triangle being preferred. The preferred length (l) of the hypotenuse is approximately 2 inches, but include lengths of less than 1 inch and up to about 3 inches. The appliance includes a top surface (7) and bottom surface (8) (not shown) having an adhesive surface covered with a peel-away layer (9) (not shown).

FIG. 3 Embodiments

Figure 3:
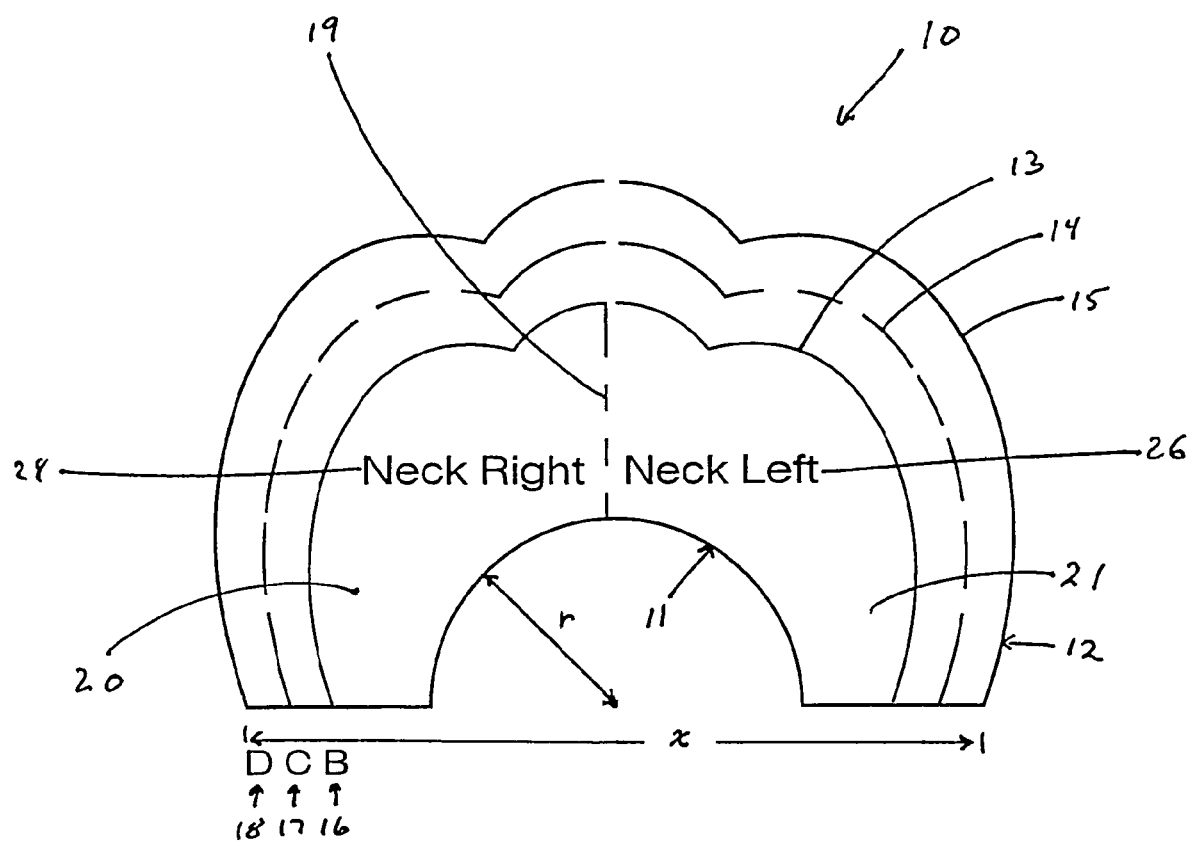

An example of a preferred embodiment of the appliance intended for use in lifting and supporting the breasts and for lifting the nipple area of the breast is shown in FIG. 3. With reference to FIG. 3, the appliance (10) has a generally semi-annular shape, with the inner perimeter of the annulus (11) preferably semi-circular with a radius of curvature (r), and the outer perimeter of the annulus (12) preferably having a curved border, composed of one or more curves. The preferred radius (r) of the inner perimeter (11) is approximately 1 inch, but includes a range of radii of about 0.5 inch to about 1.5 inches. The width (x) across the base of the semi-annular shape may vary from about 3 inches to about 6 inches to allow for differing breast size. The appliance (10) includes outlines (13,14,15) to provide for adjustment of the overall size of the appliance by cutting along the outline. The outlines (13,14,15) may be designated by letters B (16), C (17) and D (18) corresponding to the user's bra cup size. The appliance includes an outline (19) which divides the "B" bra cup size appliance into equal and symmetrical pieces or halves, which are designated "Neck Right" (24) and "Neck Left" (26), respectively. The appliance includes a top surface (22) (not shown) and bottom surface (20) having an adhesive surface covered with a peel-away layer (21) upon which outlines (13,14,15,19) may be displayed.

Use of Preferred Embodiments

A preferred method of using the appliance (10) includes the following steps. The appliance is cut to the user's appropriate bra cup size, if desired. All or a portion of the peel-away layer is removed from the adhesive surface of the appliance. The appliance is applied with the adhesive surface in contact with the skin of the upper surface of the breast so that the inner perimeter (11) of the semi-annulus is adjacent to the areola, and is adhered in that location. The thus partially applied appliance (10) is gently moved generally upwardly and/or rearwardly to lift the breast, and in particular to lift the area of the areola and nipple, to the degree desired by the user. Once the breast has been thus lifted the desired amount, the remaining portion of the appliance is adhered to the skin of the upper surface of the breast and/or chest, to maintain the breast in the desired position. If desired, at the option of the user, a second appliance may be applied similarly to the under surface of the breast to provide additional support.

A further preferred method of using the appliance (10) includes the following steps. The appliance is cut along the outline for the "B" bra cup (13) size and then is cut into equal and symmetrical left and right halves or pieces. All or a portion of the peel-away layer is removed from the adhesive surface of one of the two equal pieces of the appliance, and is applied with the adhesive surface in contact with the skin of the side of the neck below and/or behind the ear where it is partially adhered to the skin. The thus partially applied appliance piece is gently moved generally upwardly and/or rearwardly to lift skin and tissue of the throat and under the chin, to the degree desired by the user. Once the skin and tissue has been thus lifted the desired amount, the remaining portion of the appliance piece is adhered to the skin of the side of the neck, to maintain the skin in the desired position. The procedure is then repeated with the second half or equal piece of appliance (10) on the opposite side of the neck Yet another preferred method of using the appliance (10) includes the following steps. The appliance is cut along the outline for the "B" bra cup (13) size and then is cut into equal and symmetrical left and right halves or pieces along line (19). All or a portion of the peel-away layer is removed from the adhesive surface of each of the two equal pieces of the appliance, and each piece is applied to opposite sides of the neck, with the adhesive surface in contact with the skin of the neck below and/or behind the ear, below the hairline, where each piece in turn is partially adhered to the skin. The thus partially applied appliance pieces are gently moved generally upwardly and/or rearwardly toward each other, to lift the skin and tissue of the throat and under the chin, to the degree desired by the user. Once the skin and tissue has been thus lifted the desired amount, the remaining portion of each appliance piece is adhered to the skin of the rear and/or side of the neck, to maintain the skin in the desired position.

A preferred method of using the appliance (6) includes the following steps. All or a portion of the peel-away layer is removed from the adhesive surface of the appliance. The appliance is applied with the adhesive surface in contact with the skin of the side or back of the neck, below the hairline, and is partially adhered in that location. The thus partially applied appliance (6) is gently moved generally upwardly and/or rearwardly to lift skin and tissue of the throat and under the chin, to the degree desired by the user. Once the skin and tissue has been thus lifted the desired amount, the remaining portion of the appliance is adhered to the skin of the side of the neck, to maintain the skin in the desired position. The procedure is then repeated with a second appliance (6) on the opposite side of the neck A preferred method of using the appliance (1) includes the following steps. All or a portion of the peel-away layer is removed from the adhesive surface of the appliance. The appliance is applied with the adhesive surface in contact with the skin of the forehead above the eyebrow, and is partially adhered in that location. The thus partially applied appliance (1) is gently moved generally upwardly to lift skin and tissue above and adjacent to the eyebrow, thus lifting the eyebrow and eyelid to the degree desired by the user. Once the skin and tissue has been thus lifted the desired amount, the remaining portion of the appliance is adhered to the skin of the forehead preferably adjacent to the hairline. The procedure is then repeated with additional appliances (1) for the same eyebrow or the other eyebrow as desired by the user.

I claim:

1. A method of lifting a human breast and holding the breast in an elevated position comprising:
    providing a flexible sheet made of translucent material, cut into a predetermined shape and having an adhesive on one side of the sheet to form an adhesive surface having a first portion and a remaining portion;
    applying the first portion of the adhesive surface of the sheet to skin of the upper surface of the breast adjacent the breast areola to adhere the first portion of the adhesive side of the sheet to the breast;
    moving the sheet upwardly to lift the sheet and the breast to an elevated position; and,
    applying the remaining portion of the adhesive surface of the sheet to the skin of the upper surface of the breast to adhere the sheet to the skin of the upper surface of the breast and to hold the breast in the elevated position.

2. The method of claim 1 including the step of providing a peel-away layer covering the adhesive surface.

3. The method of claim 2 including removing the peel-away layer from the adhesive surface prior to applying the first portion of the adhesive surface to the skin of the upper surface of the breast.

4. The method of claim 2 including removing a portion of the peel-away layer from the adhesive surface prior to applying the first portion of the adhesive surface to the skin of the upper surface of the breast.

5. Temporarily lifting and smoothing the skin of a human breast comprising the method steps of:
    exposing a human breast having a top surface;
    providing a sheet made of a translucent material with a bottom surface having an adhesive thereon;
    adhering the bottom adhesive surface of the translucent sheet on to the top surface of the breast;
    lifting the breast upwardly and adhering the adhesive onto the skin surface of the breast at a higher position on the breast thereby temporarily maintaining, when the human is standing or sitting upright, the breast at a lifted position that is higher than a position of the breast prior to adhering the sheet to the top surface of the breast; and,
    the sheet temporarily maintaining skin of the top surface of the breast in a condition relatively smoother than the condition of the skin of the top surface of the breast prior to adhering the sheet to the top surface of the breast.

* * * * *